(12) United States Patent
Morschbacker (10) Patent No.: US 8,222,354 B2
(45) Date of Patent: Jul. 17, 2012

(54) INTEGRATED PROCESS FOR THE PRODUCTION OF ETHYLENE-BUTYLENE COPOLYMER, AN ETHYLENE-BUTYLENE COPOLYMER AND THE USE OF ETHYLENE AND 1-BUTYLENE, AS COMONOMER, SOURCED FROM RENEWABLE NATURAL RAW MATERIALS

(75) Inventor: Antonio Luiz Ribeiro de Castro Morschbacker, Porto Alegre (BR)

(73) Assignee: Braskem S.A., Camacari (BR)

( * ) Notice: Subject to any disclaimer, the term of this patent is extended or adjusted under 35 U.S.C. 154(b) by 165 days.

(21) Appl. No.: 12/673,421

(22) PCT Filed: Dec. 5, 2008

(86) PCT No.: PCT/BR2008/000372
§ 371 (c)(1),
(2), (4) Date: Feb. 12, 2010

(87) PCT Pub. No.: WO2009/070858
PCT Pub. Date: Jun. 11, 2009

(65) Prior Publication Data
US 2011/0213104 A1    Sep. 1, 2011

(30) Foreign Application Priority Data
Dec. 5, 2007  (BR) .................................... 0704605

(51) Int. Cl.
*C08F 2/00* (2006.01)
*C08F 16/34* (2006.01)
*C08F 210/00* (2006.01)
(52) U.S. Cl. ................. 526/75; 526/315; 526/348
(58) Field of Classification Search ............... 526/75, 526/315, 348
See application file for complete search history.

(56) References Cited

U.S. PATENT DOCUMENTS

| 4,539,293 A | 9/1985 | Bergstrom et al. |
| 4,857,611 A * | 8/1989 | Durand et al. ............... 526/88 |
| 5,753,474 A | 5/1998 | Ramey |
| 6,242,662 B1 | 6/2001 | Dorbon et al. |

FOREIGN PATENT DOCUMENTS

| GB | 1204863 A | 9/1970 |
| WO | WO-2004/078336 A2 | 9/2004 |

OTHER PUBLICATIONS

Olson et al., "Higher-Alcohols Biorefinery," Applied Biochemistry and Biotechnology, Humana Press, Inc, US, vol. 113-116, pp. 913-932, Jan. 1, 2004, XP007907768.

* cited by examiner

*Primary Examiner* — William Cheung
(74) *Attorney, Agent, or Firm* — Birch, Stewart, Kolasch & Birch, LLP (57) ABSTRACT

The present invention relates to integrated processes for the production of ethylene-butylene copolymers from at least one renewable natural raw material. More specifically, the present invention relates to processes wherein in the ethylene monomer, used in the polymerization for the production of an ethylene copolymer, and the 1-butylene, as the comonomer, is obtained by the ethanol dehydration reaction, which ethanol is produced by the fermentation of sugars, and the 1-butylene comonomer is obtained according to at least one of the following reactions: (i) dehydration reaction of 1-butanol directly produced by the fermentation of sugars, (ii) dehydration reaction of 1-butanol obtained from ethanol via a chemical route, which ethanol is produced by the fermentation of sugars; and/or (iii) dimerization reaction of ethylene produced by the dehydration of ethanol obtained from the fermentation of sugars, followed by isomerization of the 2-butylene isomers then formed.

The ethylene-butylene copolymer thus produced is completely based on carbon atoms originated from renewable natural raw materials and, upon incineration it produces $CO_2$ from a non-fossil origin.

18 Claims, 3 Drawing Sheets

INTEGRATED PROCESS FOR THE PRODUCTION OF ETHYLENE-BUTYLENE COPOLYMER, AN ETHYLENE-BUTYLENE COPOLYMER AND THE USE OF ETHYLENE AND 1-BUTYLENE, AS COMONOMER, SOURCED FROM RENEWABLE NATURAL RAW MATERIALS

FIELD OF THE INVENTION

The present invention relates to integrated processes for the production of ethylene-butylene copolymers from at least one renewable natural raw material. More specifically, the present invention relates to processes wherein the ethylene monomer, used in the polymerization for the production of a copolymer of ethylene and 1-butylene, as the comonomer, is obtained by the ethanol dehydration reaction, which ethanol is produced by the fermentation of sugars, and the 1-butylene is obtained according to at least one of the following reactions: (i) dehydration reaction of 1-butanol directly produced in the fermentation step of sugars, (ii) dehydration reaction of 1-butanol obtained from ethanol via a chemical route, which ethanol is produced by the fermentation of sugars; and/or (iii) dimerization reaction of ethylene produced by the dehydration of ethanol obtained from the fermentation of sugars, followed by isomerization reaction of the 2-butylene isomers then formed.

The ethylene-butylene copolymer thus produced is completely based on carbon atoms originated from renewable natural raw materials and, upon incineration it produces $CO_2$ from a non-fossil origin.

DISCLOSURE OF THE STATE OF THE ART

The many different types of polyethylenes encompass the most widely produced and used thermoplastic resin in the world. These are obtained through the homo-polymerization of ethylene or the copolymerization of ethylene and at least one comonomer, the most widely used ones being 1-butylene, 1-hexene and 1-octene (LLDPE, Andrea Borruso, CEH-2007, Chemical Economics Handbook-SRI International).

One of the most important polyethylene grades is the linear low density polyethylene (LLDPE). However, further there are the high density, the medium density and the very low density copolymers.

The LLDPE has a large range of applications, especially in the production of flexible packaging. Among its main uses there are the production of packaging films, industrial bags, sanitary napkins, frigorific packaging and a wide collection of other products.

On their turn, as an example, the high density polyethylenes find widespread application in the manufacture of films and of parts made by injection and blow molding processes; medium density polyethylenes are used in industrial thermoplastic transformation process known as "rotational molding", while very low density polyethylenes are used in the lining of carton packaging and in adherent lining layers.

The ethylene is an olefin mainly produced as a by-product of oil refining, through vapor reforming or catalytic cracking processes. Another route used for the ethylene production is the recovery and dehydrogenation of the ethane present in natural gas.

The 1-butylene also is an olefin, which production is equally based on fuel derivatives, as well.

The conventional routes used for the production of both these olefins are evaluated in the following studies: "Ethylene", Michael T. Devanney, CEH Marketing Research Report-2005, SRI International, and "Butylenes", Edward R. Sporcic, Masahiro Yoneyama, Loon-Ling Ring, CEH, Marketing Research Report-2005, SRI International.

On its own right, global interest on organic products from renewable sources has greatly grown in the last few years, especially in the case of plastics. The use of products derived from natural sources, as opposed to those obtained from fossil sources, as raw material, has increasingly been a widely preferred alternative, as an effective means of reducing the atmospheric carbon dioxide concentration increase, therefore effectively preventing the expansion of the so called greenhouse effect.

Products thus obtained from natural raw materials have a differential, relative to fossil sourced products, which is their renewable carbon contents. This renewable carbon content can be certified by the methodology described in the technical ASTM D 6866-06 Norm, "Standard Test Methods for Determining the Biobased Content of Natural Range Materials Using Radiocarbon and Isotope Ratio Mass Spectrometry Analysis".

Besides that, products obtained from renewable natural raw materials have the additional property of being able to be incinerated at the end of their life cycle, whereas only producing $CO_2$ of a non-fossil origin.

The most widely known examples of industrial products, among those obtained from natural sources, are the natural origin fuels, such as the bioethanol and the biodiesel. Other alternatives already available in the market are the biopolymers, such as poly-lactic acid, and poly-hydroxy-butirate, which can be obtained from sugars sources. Biopolymers display a large growth potential, even if they still have limiting physical properties and higher production costs, thus hindering their more widespread application. Further information can be obtained in "Biodegradable Polymers", Gregory M. Bohlmann, CEH, Marketing Research Report-2004, SRI International.

Biologically sourced ethanol, known as bio-ethanol, is obtained by the fermentation of sugars derived from cultures such as that of sugar cane and beets, or from hydrolyzed starch, which is, in turn, associated with other cultures such as corn. An alternative, currently under development, is the use of hydrolysis based products from cellulose and hemi-cellulose, which can be found in many agricultural by-products, such as straw and sugar cane husks. This fermentation is carried out in the presence of varied microorganisms, the most important of such being the yeast *Saccharomyces cerevisiae*.

Another primary alcohol, 1-butanol, further can be directly produced by the fermentation of sugars (including starch and cellulose) using *Clostridium* gender bacteriae, such as the *Clostridium acetobutylicum* species. The use of these bacteriae in sugars fermentation based 1-butanol production processes is known as the Weizmann process, and it has been known for almost 100 years.

Other well known 1-butanol production routes are disclosed in U.S. Pat. No. 4,539,293 and U.S. Pat. No. 5,753,474. In the processes disclosed in those patent documents, sugars are initially used in the production of butyric acid, which is later converted into 1-butanol. Other products commercially obtained by means of fermentation processes are, for instance, lactic acid, acetone, and even polymers such as the poly-hydroxy-alcanoates.

Ethylene production from ethanol dehydration is a widely known process and was commercially implemented in a few industrial units. In this process, ethanol is converted into ethylene by means of a catalytic reaction at temperatures usually above 300° C. A large variety of catalysts can be used for this purpose, but the most commonly used type consists of high specific surface area gamma-alumina. Further details about this technology can be found in the following study: "Ethylene from Ethanol", Harold W. Scheeline and Ryoji Itoh, PEP Review 79-3-4, January 1980, SRI International, and also in U.S. Pat. No. 4,232,179, U.S. Pat. No. 4,234,752, U.S. Pat. No. 4,396,789 and U.S. Pat. No. 4,529,827, as well as in the patent application WO 2004/078336.

The production of butylenes from 1-butanol is not commercially being used until this moment. Documents US 2008/0015395A1 and US 2008/0045754A1 disclose the production of butylenes mixtures in the presence of acid catalysts, but no information about the butylene isomers produced is provided. Besides that, the processes described in those documents are low butylene yield ones, due to low conversion and/or low selectivity, however not describing the by-products then formed.

The articles of Macho, V. et al (Dehydration of C4 alkanols conjugated with a positional and skeletal isomerization of the formed C4 Alkenes. Applied Catalysis A: General 214; 2001; 251-254. Elsevier) and Ashour, S. (Factors affecting the activity and selectivity of alumina catalysts in the dehydration of 1-butanol. Adsorption Science and Technology Vol. 22, N° 6; 2004) discloses the dehydration of anhydrous 1-butanol under isothermal conditions, in the presence of alumina based catalysts. The article of Ceckiewicz, S. et al (Catalytic Reactivity of Phosphates with 1-Butanol, Pure and in a mixture with acetone, ethanol, acetic acid and water. Bull. Soc. Chim. Belg.; Vol. 96; n° 4; 1997) discloses the dehydration of anhydrous 1-butanol and in the presence of water, under isothermal conditions, in the presence of some catalysts, such as gamma-alumina. According to the cited articles, mixtures of products are obtained. Temperatures around 200° C. to 250° C. show low conversions and favor the formation of di-butyl-ether, while temperatures ranging from 400° C. to 470° C. favor the formation of isobutylene. The reactions disclosed in such articles result in low conversion and/or low selectivity towards n-butylenes.

Other examples of alcohols dehydration are described in U.S. Pat. No. 4,234,752, and in documents WO 2004/078336A2 and GB 576480A.

Nevertheless, in spite of the many advances in the biopolymers field, to the current date, there is no document describing the production of an ethylene-butylene copolymer via the polymerization of ethylene and 1-butylene fully made from at least one renewable natural raw material. Bio-polyethylenes so produced display low production costs and properties, which are proven to be suitable for a wide range of applications.

OBJECTIVES OF THE INVENTION

Bearing in mind the outlook above mentioned, it is an objective of the invention to provide integrated processes for the production of ethylene-butylene copolymers, in which both monomers are entirely based on at least one renewable natural raw material.

Another objective of the invention is to provide ethylene-butylene copolymer production processes that use 1-butylene as the comonomer, wherein the ethylene is obtained from the ethanol dehydration reaction, which ethanol is produced by the fermentation of sugars, and the 1-butylene comonomer is obtained according to at least one of the following reactions: (i) dehydration reaction of 1-butanol directly produced by the fermentation of sugars, (ii) dehydration reaction of 1-butanol obtained from ethanol via a chemical route, which ethanol is produced by the fermentation of sugars; and/or (iii) dimerization reaction of ethylene produced by the dehydration of ethanol obtained from the fermentation of sugars, followed by isomerization reaction of the 2-butylene isomers thus formed.

A further objective of the present invention is to provide ethylene-butylene copolymers production processes, wherein the product of any of the abovementioned reactions i, ii, iii is treated to separate the 1-butylene from the 2-butylene isomers, isobutylene, di-butyl ether, CO, $CO_2$, and other possible impurities, followed by further selective isomerization reaction of cis-2-butylene and trans-2-butylene isomers to 1-butylene.

Another objective of the present invention is to provide ethylene-butylene copolymers production processes, wherein the units of such processes are completely integrated, and thus the processes are of low cost, simple operation and versatile due to the alternatives and interconnections within their steps. The new integrated processes are highly energy and materials efficient, and, as such, they yield high productivities.

It is another objective of the present invention to provide ethylene-butylene copolymers, the 1-butylene as the comonomer, produced entirely from renewable natural raw materials, which will comprise carbon, which is 100% from renewable origin, according to certification provided by the essay method described in the technical ASTM D 6866-06 Norm.

It is also an objective of the present invention the use of ethylene and 1-butylene, sourced exclusively from natural renewable carbon raw materials, for the production of ethylene copolymers. As a consequence of such, the ethylene-butylene copolymer of the present invention has the additional property of generating non fossil origin $CO_2$ upon incineration.

The products thus obtained from the present invention, in the course of their life cycle, favor the reduction of the emission of gases responsible for the so called "greenhouse effect", which are normally generated by the incineration of fossil origin based polymeric materials.

SUMMARIZED DISCLOSURE OF THE INVENTION

The present invention refers to integrated processes for the production of ethylene-butylene copolymers, which use 1-butylene as the comonomer, wherein the ethylene and 1-butylene are obtained from renewable raw materials.

The processes of the present invention for producing of ethylene-butylene biocopolymers are simple low cost ones, and can be advantageously installed in locations where there is large availability of starch rich renewable natural raw materials, such as corn, or cellulose and hemicellulose rich ones, contained in lignocellulosic materials, and/or, preferably, sugars rich materials, such as sugar cane.

The ethylene used in the present invention is obtained by the dehydration of its respective alcohol, the ethanol, obtained via fermentation. The 1-butylene comonomer can be obtained according to at least one of the following steps: (i) dehydration of 1-butanol directly produced by the fermentation of sugars; (ii) dehydration of 1-butanol obtained from ethanol via a chemical route, which ethanol is produced by the fermentation of sugars, and/or (iii) dimerization of ethylene produced from the ethanol dehydration step, the ethanol being obtained from the fermentation of sugars, followed by isomerization of the 2-butylene isomers thus formed.

The integrated processes of the present invention are also characterized by showing a high degree of energy and materials efficiency on a global balance, as well as high productivity.

Organic products made from renewable raw materials such as, for example, the copolymers of the present invention, are an effective way of contributing to the reduction of the amount of atmospheric $CO_2$, in the case these polymeric products are incinerated at the end of their life cycles.

The ethylene-butylene copolymer of the present invention is obtained by the polymerization of the mentioned monomers, in the presence of a Ziegler-Natta or metallocene type catalyst, among others.

The renewable sourced copolymer production processes of the present invention encompass low cost ethylene and 1-butylene production steps, from renewable raw materials. The use of these monomers in the production of ethylene-butylene copolymers, according to the present invention, leads to the production of a bio-copolymer, which was certified according to the essay method of the technical ASTM D 6866-06 Norm as having 100% carbon content from renewable sources.

DESCRIPTION OF THE FIGURES

The advantages and features of the present invention will be more evident through the disclosure of the preferred embodiments, herein given in the manner of example and not limiting in any way, and through the figures to which they refer.

DETAILED DESCRIPTION OF THE INVENTION

The present invention disclosed integrated processes for the production of ethylene-butylene copolymers, wherein the ethylene monomer is obtained by the dehydration reaction of its respective alcohol, ethanol, which in turn is obtained by the fermentation of sugars; and the 1-butylene comonomer is obtained according to at least one of the following reactions: (i) dehydration of 1-butanol directly produced by the fermentation of sugars, (ii) dehydration of 1-butanol obtained from ethanol via a chemical route, which ethanol is produced by the fermentation of sugars, and/or (iii) dimerization of ethylene produced by the dehydration of ethanol obtained from the fermentation of sugars, followed by isomerization of the 2-butylene isomers then formed.

Throughout the present text, it is to be understood by the term "sugars", the dissolved sugars coming, for instance, from sugar cane juice (containing saccharose, glucose and fructose), or a hydrolyzed starch product (containing glucose), or hydrolyzed lignocellulosic components (containing mainly glucose and, to a lesser extent, xylose and galactose, among others).

Sugar cane, beets, corn, manioc, cellulose and hemicellulose are non limiting examples of renewable raw materials for use in the present invention.

The ethylene-butylene copolymer of the present invention consists of a copolymer of ethylene and 1-butylene as comonomer, in which the comonomer mass percent content is in the range from 0.5% to 30%, preferably from 2% to 20%, in such a way that this concept not only applies to linear low density polyethylene, but also to very low, medium and high density ethylene-1-butylene copolymers, which display densities between 0.900 and 0.960 g/cm3.

The ethylene-butylene copolymers production processes of the present invention, are simple, low cost ones, and can be advantageously installed in locations where there is large availability of starch rich renewable natural raw materials, such as corn, or cellulose and hemicellulose rich ones, contained in lignocellulosic materials, and/or preferably rich in sugars, such as sugar cane. Optionally, other renewable natural raw materials can be used as sugars sources, such as beet, and as starch sources, such as manioc, among others.

In Brazil, the mainstream ethanol production processes use sugar cane as raw material. After being harvested, the sugar cane is shipped on flat racks, in the form of bundles, thus being trucked to the sugar and/or alcohol plant for further processing.

In the processes of the present invention, sugar cane (1*a*), for example, is transported to the grinding or diffusion and filtration unit (1), for sugar cane juice (2*a*) extraction with water (1*b*) and the production of sugar cane husks (12*a*), as a by-product. The sugar cane juice (2*a*) thus obtained, after undergoing the suitable purification treatment, is sent to the production of ethanol and/or 1-butanol, a portion of the sugar cane juice possibly going to a sugar production plant and another portion to the production of other derivatives. The fermentation of the sugar cane juice in vats (2,3) is preceded by a sugars concentration adjustment step, as well as a step to adjust the medium pH, and to add nutrients.

When corn is used as a raw material, it is treated in a similar processing way as that of sugar cane. The starch rich corn grain is ground and then subjected to a hydrolysis step, thus producing a glucose rich medium, to which nutrients are added. It is then ready for the production of ethanol and/or other fermentation products.

The use of lignocellulosic materials, such as, for instance, husks and sugar cane leaves, require a more rigorous hydrolysis step, the subsequent fermentation being carried out by means of microorganisms able to ferment other types of sugars besides glucose.

An alternative related to the present integrated process is the use of sugar cane husks for supplying the energy to be used in the subsequent processes, in such a way as to integrate them from an energy standpoint, thus making it possible to obtain a final product using renewable raw materials as well as renewable energy sources, therefore having superior value.

In a preferred embodiment of the invention, the raw material comprises sugars rich materials, and the yeast *Saccharomyces cerevisiae* is used as the fermentation agent, producing ethanol, as the final product, and carbon dioxide ($CO_2$), as the main by-product. Other types of microorganisms can be alternatively used in the fermentation process.

In the case of ethanol production, the leavened must (3*a*), coming from the fermentation step (FIGS. 1 and 2), is then treated in a distillation process in distiller (4), for the production of hydrated ethanol (4*a*). The distillation bottoms, called vinhoto (12*b*), is rich in nutrients and can be sent to a waste treatment unit (19), or, preferably, can be used in the irrigation of the sugar cane production fields. It is understood by "distiller" the array of one or more distillation columns set up in such a way as to purify the process streams.

Figure 1:
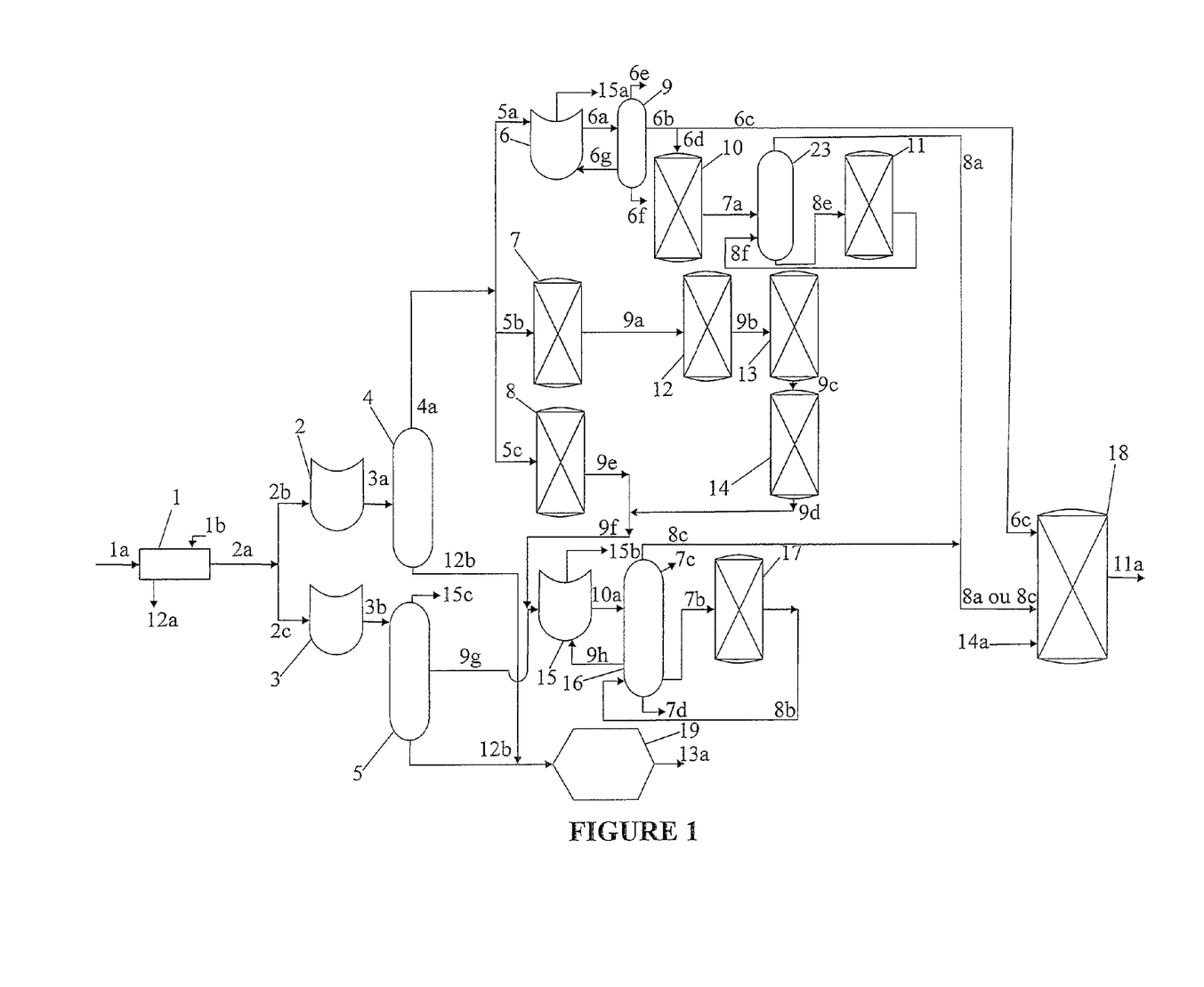
FIG. 1 shows a simplified integrated plant of one of the ethylene-butylene biocopolymer production processes of the present patent application, for example, based on sugar cane, wherein the ethanol and the 1-butanol are dehydrated in separated steps.
Figure 2:
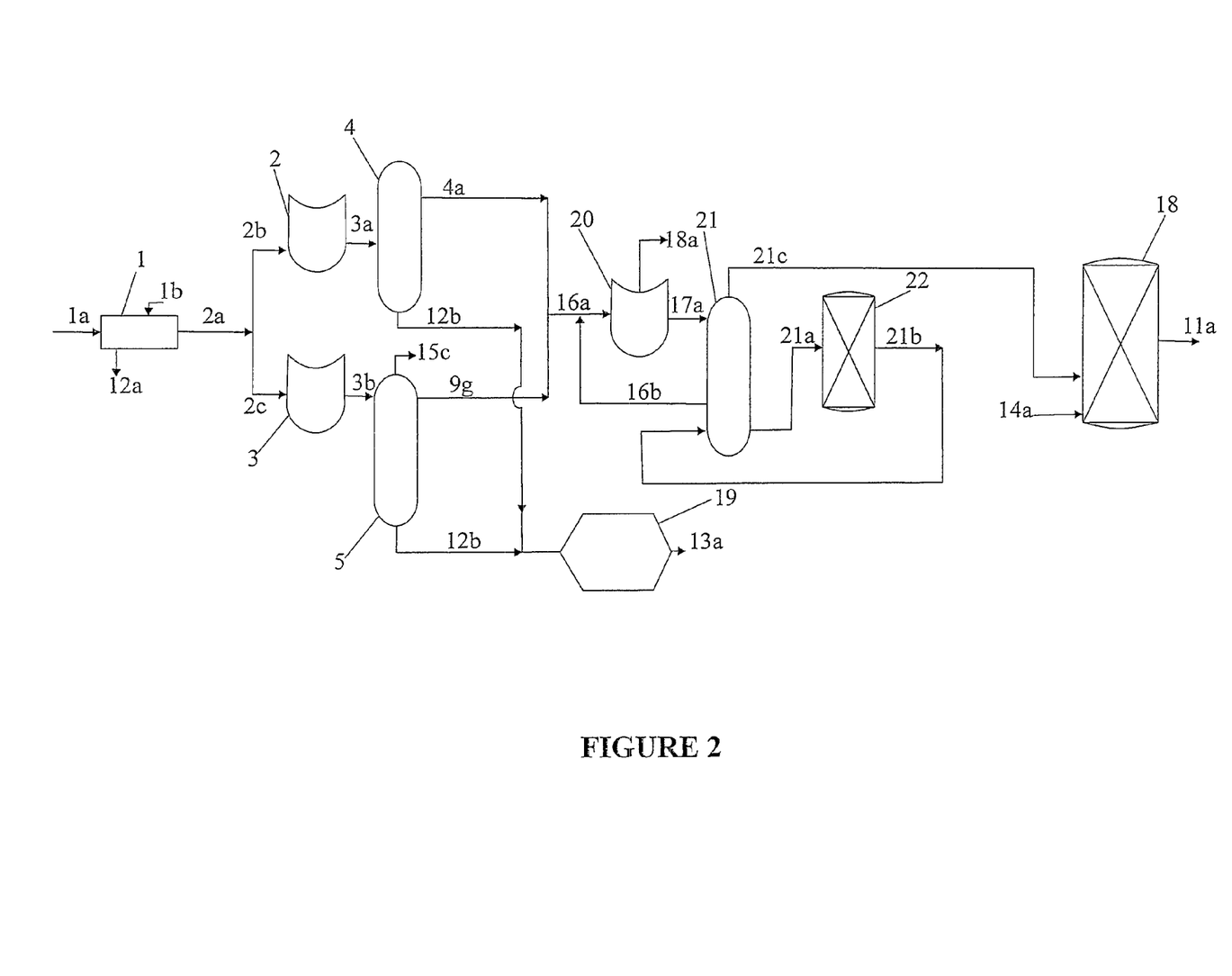
FIG. 2 shows a simplified integrated plant of another ethylene-butylene bio-copolymer production process of the present patent application, for example, based on sugar cane, wherein the ethanol and the 1-butanol are simultaneously dehydrated.

Preferably, the processes of the present invention can be adjusted in such a way as for the water to ethanol molar ratio to be equal to that required at the admittance to the dehydration reactor (6), where the ethylene stream (6a) will be produced, as shown on FIG. 1, or to the dehydration reactor (20) for the production of the ethylene and 1-butylene stream (17a), as shown on FIG. 2. Optionally, this ethanol (4a) can be treated by any of various drying processes known to the art, so that anhydrous alcohol can be obtained.

As regards 1-butanol, it can be obtained either by the fermentation of sugars in vats (3), or via a chemical route starting with ethanol (4a), through aldolic condensation, in the condensation reactor (12), of the acetaldehyde produced via the controlled oxidation (dehydrogenation) of ethanol (5b) in reactor (7), or through direct 1-butanol synthesis from ethanol (5c), in the direct synthesis reactor (8), which the sole by-product is water, according to the method described in the patent application EP 1829851.

The production of 1-butanol directly from sugars fermentation is similar to that of ethanol, as previously mentioned, using different species of the gender *Clostridium*, such as *C. acetobutylicum, C. butylicum, C. beijerinckii, C. aurantibutyricum, C. pasteurianum, C. sporogenes, C. cadaveris.*

The 1-butanol is the main product from such a fermentation, but substantial amounts of other products such as acetone, iso-propanol, ethanol and carbon dioxide ($CO_2$) are also obtained as by-products. These products are separated and purified through the usual distillation techniques.

A preferred process for the production of 1-butanol is carried out in two steps, the first one being a sugars fermentation, mainly poly-saccharides, which are converted mainly into butyric acid, and other acids, by the microorganisms activity, in vats (3). In the following step, the acids are transferred to a second stage, operating at different conditions, including the use of microorganisms different from those used in the first stage, with the sole function of converting the acid to a solvent (solvatogenesis), thus producing 1-butanol continuously, in a stable process, and achieving high yields, as described in U.S. Pat. No. 5,753,474. Further details are disclosed in the following studies: "*Acetone, Isopropanol and Butanol Production by Clostridium beijerinckii (syn. Clostridium butylicum) and Clostridium aurantibutylicum*", George et al.; Applied and Environmental Microbiology, American Society for Microbiology; 1983, "Acetone-Butanol Fermentation Revisited", D. T. Jones et al., Microbiological Reviews, American Society for Microbiology; 1986 and Encyclopedia of Bioprocess Technology—Fermentation, Biocatalysis and Bioseparation, Flickinger, Michael C.; Drew, Stephen W., 1999 John Wiley & Sons.

The 1-butanol can also be obtained from ethanol via a chemical route, either directly from ethanol (5c) through contacting catalysts in reactor (8), such as, for instance, calcium phosphates based catalysts (as described in patent application EP 1829851), or indirectly, in a sequence of steps in reactors (7, 12 13, 14): dehydrogenation of ethanol thus forming acetaldehyde, aldolic condensation of said acetaldehyde forming 3-hydroxy-butanal, in the presence of catalysts, such as calcined MgAl hydrotalcites, followed by dehydration with the formation of crotonaldehyde, and further hydrogenation with the formation of 1-butanol, as shown on FIG. 1.

The process for preparing ethylene from ethanol produced from a renewable natural source is carried out via dehydration of ethanol in reactor (6), in the presence of catalysts, such as alumina, silica, silico-alumina, zeolites, and other metallic oxides, at temperatures ranging from 180° C. to 600° C., preferably ranging from 300° C. to 500° C., as mentioned in U.S. Pat. No. 4,232,179. The reaction is carried out in an adiabatic or isothermic, fluidized or fixed bed reactor.

The contaminants generated in the process are removed by means of a train of purification columns, traditionally used for this kind of reaction (not depicted on the figures of the present invention). Ethylene then passes through washing columns and beds for the removal of acids, such as acetic acid, water removal and polar compounds, as well as carbon monoxide and dioxide.

Ethylene, as per the present invention, can be produced by known processes, such as those described in the article titled "Ethylene from Ethanol", Harold W. Scheeline and Ryoji Itoh, PEP Review 79-3-4, January 1980, SRI International and U.S. Pat. No. 4,234,752, U.S. Pat. No. 4,396,789 and U.S. Pat. No. 4,529,827; and in patent application WO 2004/078336 A2.

The 1-butanol dehydration initially produces 1-butylene. However, since both the catalysts and the operating conditions normally adopted for the dehydration reaction are capable of inducing the isomerization of the 1-butylene forming into both the two geometric 2-butylene isomers, it was found that the exit stream (10a) from dehydration reactor (15), as show on FIG. 1, is formed by a mixture of 1-butylene, cis-2-butylene and trans-2-butylene. The composition of this mixture will depend on the chosen process conditions, such as temperature, 1-butanol:water reactor feed ratio, residence time and type of catalyst used.

The dehydration reaction is conducted in the presence of catalysts, such as alumina, silica, silico-alumina, zeolites, and other metallic oxides, being carried out in an adiabatic or isothermic, fluidized or fixed bed reactor.

In the present process, the 1-butanol alcohol (9g) dehydration step for the production of 1-butylene is optimized by means of operating with residence times that range from 0.1 to 60 seconds, preferably from 1 to 30 seconds, and temperatures varying from 150° C. to 380° C., preferably from 250° C. to 370° C., the unreacted 1-butanol (9h) being recovered and recycled into the dehydration reactor (15) feed, as seen on FIG. 1.

Optionally, the dehydration reaction of 1-butanol alcohol in reactor (15) can be carried out under the conditions already mentioned, the reactor outlet stream (10a) from reactor (15), containing 2-butylene isomers contaminated 1-butylene is later submitted to a purification process, such as, for example, distillation, followed by an isomerization step of the 2-butylenes (7b) into 1-butylene.

The dehydration product purification step, for obtaining the pure 1-butylene, when taken, happens by feeding the dehydration reactor (15) outlet stream (10a) to a distillation zone, in distiller (16), connected to an isomerization step, in reactor (17), in the presence of hydrogen, as described in U.S. Pat. No. 6,242,662, or in the presence of basic catalysts or zeolites, as described on item g) of patent application US 2207/0055088.

The contaminants produced in the 1-butanol dehydration step are removed by means of a train of purification columns similar to the one used in the production of ethylene from ethanol. The 1-butylene then passes through beds for the removal of acids, such as butyric acid, water and polar compounds, as well as carbon monoxide and dioxide (not depicted on the figures of the present invention).

One common feature related to the dehydration processes is the generation of water as a by-product (streams 15a, 15b, 18a). Water is an ever scarcer natural resource. Its availability in certain regions of the planet, even in areas used in the production of certain renewable agricultural raw materials, is ever more valuable, and its use must be managed in such a way as to avoid losses, as well as to recycle volumes which are present in effluent streams. The water generated in the process and eliminated in streams 15a, 15b and 18a can be recycled into the process, for instance, to the extraction step of the sugar cane comprising grinding and diffusion steps.

In another embodiment of the present invention, as shown on FIG. 2, the dehydrations of ethanol and 1-butanol alcohols obtained from renewable raw materials, is carried out simultaneously. In the process described in the present invention, the alcohols can be jointly fed to reactor (20) containing catalysts, such as alumina, silica, silico-alumina, zeolites, and metallic oxides, at temperatures ranging from 150° C. to 380° C., and preferably from 250° C. to 370° C., and residence times varying from 0.1 to 60 seconds, and preferably from 1 to 30 seconds. The reaction is carried out in adiabatic or isothermic, fluidized or fixed bed reactors, preferably in fluidized bed isothermic reactors. The ethanol/butanol ratio will be adjusted according to the ethylene/1-butylene ratio required at the ethylene-1-butylene copolymer polymerization reaction.

In the olefins production processes previously described, as well as in the present processes, the alcohols can be fed to the reactors in the presence of water or anhydrously, the water present in the feed stream of the dehydration reactor promotes the maintenance of heat inside the reactor, enhancing the selectivity of the reaction towards the ethylene and 1-butylene monomers, and reducing coke formation. The water/ethanol and water/butanol ratios, in the processes of the present invention, may vary from 0:1 to 20:1, preferably from 0.2:1 to 10:1.

Alternatively, 1-butylene from a renewable raw material is synthesized, in the dimerization and isomerization reactors (10,11), by the dimerization of ethylene (6d), obtained from ethanol (5a), in the presence of nickel complexes, as described in patent GB 1204863, mainly forming a 2-butylene geometric isomers mixture (7a), followed by isomerization of these 2-butylene isomers into 1-butylene, in the presence of hydrogen, as described in U.S. Pat. No. 6,242,662, or in the presence of basic catalysts or zeolites, as described on item g of patent application US 2007/0055088.

Another relevant aspect of the present invention resides in the fact that in the present processes for the production of ethylene-butylene copolymers, the ethylene and 1-butylene monomers, previously described, come entirely from renewable natural sources.

The production of the ethylene-butylene copolymers (11a) of the present invention is achieved in reactor (18), and can be carried out in a solution polymerization process, at temperatures in the range of from 105° C. to 300° C.; in a suspension polymerization process, at temperatures ranging from 50° C. to 100° C.; or in a gas phase polymerization process, at temperatures ranging from 60° C. to 80° C., in the presence of catalysts, preferably Ziegler-Natta or metallocene ones.

The ethylene-butylene copolymers produced according to the processes of the present invention and, as such, being 100% renewable natural origin, effectively contribute to atmospheric $CO_2$ balance, because there will be no fossil carbon dioxide emissions in the event theses polymers are incinerated at the end of their life cycle. The carbon content from renewable natural sources present in the copolymers of the present invention is 100%, and can be certified by the essay method of the technical ASTM D 6866-06 Norm.

More specifically, in a more encompassing view of the integrated process of the present invention for the production of ethylene-butylene copolymers, in which ethanol and 1 butanol are the raw materials, the vegetal sourced raw materials (1a) are previously processed in a grinding or diffusion and filtration unit (1), for the extraction of sugars (2a), which is later fermented, thereby producing ethanol and butanol. A portion (2b) of the sugars stream (2a) is fed to vat (2), at must fermentation conditions for the production of ethanol. The ethanol containing leavened must stream (3a) is then processed in a distiller (4), for separating ethanol (4a) to be used in the production of ethylene and/or 1-butanol from vinhoto (12b). The vinhoto stream (12b) is fed to the waste treatment unit (19) and the treated waste (13a) is reused.

Ethanol from hydrated ethanol stream (4a or 5a) is dehydrated in the catalytic dehydration reactor (6) producing a not purified ethylene stream (6a), which is, in turn, purified in distillers (9), or in other additional equipment, yielding ethylene (6b or 6c) ready to be fed to polymerization reactor (18). A portion (5b) of the ethanol stream (4a) can be dehydrogenated, in the dehydrogenation reactor (7), producing an intermediate acetaldehyde stream (9a), and/or, optionally, a portion (5c) of the ethanol stream (4a) can be fed to a direct synthesis reactor (8), for directly producing the 1-butanol stream (9e) to be used in the 1-butylene synthesis.

The intermediate acetaldehyde stream (9a) from dehydrogenation reactor (7) undergoes an aldolic condensation, in the condensation reactor (12), thereby producing the intermediate 3-hydroxy-butanal exit stream (9b). The 3-hydroxy-butanal (9b) is then dehydrated, in a dehydration reactor (13), thus forming the intermediate crotonaldehyde exit stream (9c). Crotonaldehyde (9c) is hydrogenated, in hydrogenation reactor (14), finally forming 1-butanol (9d) to be used in the synthesis of 1-butylene.

Optionally, a portion (2c) of sugars stream (2a) can be fed to vats (3), at must fermentation conditions for the production of 1-butanol. The 1-butanol containing leavened must stream (3b) is distilled for separating 1-butanol (9g), to be used in the synthesis of 1-butylene, from acetone and ethanol by-products (15c) and vinhoto (12b).

Following that, 1-butanol from 1-butanol stream (9g) is dehydrated, in dehydration reactor (15), for the production of butylene isomers (10a).

The 1-butanol streams (9d and/or 9e) from the chemical syntheses, or else a mixture (9f) of those, are also dehydrated in dehydration reactor (15).

Butylene isomers stream (10a), from dehydration reactor (15), is treated in distiller (16) that separates a purified 1-butylene stream (8c), an unreacted 1-butanol recycle stream (9h), which is then returned to dehydration reactor (15), and a 2-butylene isomers stream (7b). Two by-products streams (7c and 7d) exit the distiller (16).

The 2-butylene isomers stream (7b) is fed to the isomerization reactor (17), producing 1-butylene and 2-butylene isomers mixture stream (8b).

The ethylene monomer from ethylene stream (6b or 6c) and the 1-butylene comonomer from 1-butylene stream (8c) are polymerized in the polymerization reactor (18), which is loaded with catalyst, thus producing the ethylene-butylene copolymer (11a), which has 100% carbon from renewable natural sources.

In another alternative of the integrated process of the present invention for the production of ethylene-butylene copolymers, with 1-butylene as comonomer, using ethanol as the raw material, and the ethanol being obtained from vegetable renewable sources (1a), the sugars are fermented to obtain the ethanol, without the need for the production of the intermediate 1-butanol by means of fermentation or chemical synthesis. The 1-butylene is obtained from ethylene by means of a dimerization reaction.

The vegetable sourced raw materials (1a) are processed in a grinding or diffusion and filtration unit for the production of sugars (2a), which are fed to vat (2), under ethanol producing must conditions.

The ethanol containing leavened must stream (3a) is fed to distiller (4) for separating vinhoto (12b) from ethanol (4a), to be used in the production of ethylene, which in turn will be used in the production of 1-butylene. The vinhoto stream (12b) is fed to waste treatment unit (19) and the treated waste (13a) is reused.

Ethanol from the ethanol stream (4a or 5a) is fed to dehydration reactor (6), for producing a contaminated ethylene stream (6a), which is, in turn, purified in distiller (9), and/or other equipment, forming ethylene (6b or 6c), ready to be fed to the reactor (18).

A portion (6d) of the ethylene stream (6b) is fed to dimerization reactor (10), forming a mixture of mostly 2-butylene isomers (7a). The mostly 2-butylene isomers stream (7a) is fed to isomerization reactor (11) to produce 1-butylene (8a).

Ethylene monomer from the other portion (6c) of ethylene stream (6b) and 1-butylene comonomer from 1-butylene stream (8a) are fed to and polymerized in polymerization reactor (18), which is loaded with catalyst, thus producing the ethylene-butylene copolymer (11a) having 100% carbon from renewable natural source.

In a preferred embodiment of the integrated process of the present invention, for the production of ethylene-butylene copolymer, ethanol and 1-butanol, both obtained from the fermentation in vats (2,3) and purified in distillers (4,5) form an alcohol mixture (16a), from ethanol (4a) and 1-butanol (9g) streams, and both alcohols are simultaneously dehydrated, in dehydration reactor (20), for the production of an ethylene and 1-butylene mixture (17a), water being eliminated in the exit stream (18a). The ethylene and 1-butylene mixture stream (17a) is treated in distiller (21), which outputs a first ethylene/1-butylene mixture (21c), a second 2-butylene isomers stream (21a), and another unreacted ethanol and 1-butanol recycle stream (16b), which returns to dehydration reactor (20).

The 2-butylene isomers stream (21a) is fed to isomerization reactor (22), thus forming 1-butylene/2-butylene isomers stream (21b) which returns to distiller (21).

Ethylene and 1-butylene monomers from stream (21c) are fed to and polymerized in polymerization reactor (18), which is loaded with catalyst (14a), thus producing the ethylene-butylene copolymer (11a) having 100% carbon from renewable natural sources.

Example of the Present Invention

So as to allow a better understanding of the present invention, and to demonstrate the technical improvements thus obtained, an example is presented regarding the process for obtaining the alcohols, ethanol and 1-butanol, from sugar cane treatment and then the dehydration of said alcohols for the production of monomers. All percentages indicated in the examples are mass based percentages.

Step A: Production of Ethylene

The previously obtained sugar cane juice, after undergoing filtering, cake washing and pH adjustment, was fed to fermentation vats, in a batch setup, together with a *Saccharomyces cerevisiae* inoculum. After the end of the fermentation, a leavened ethanol containing must was produced which contained 7%, by weight, of ethanol. After distillation of said must, ethanol having 92.8%, by weight, concentration was obtained.

The ethanol so produced was then fed to a dehydration system comprising 15 liter adiabatic reactors in series, each one loaded with a gamma-alumina catalyst fixed bed. In order to achieve the desired temperature of 470° C. at the entrance of the reactor, the hydrated ethanol with a water:ethanol ratio of 3:1, was previously heated. After the reaction, the output stream was purified by distillation and drying processes, obtaining polymeric grade ethylene at a 96% ethanol yield.

Step B: Production of 1-Butylene

The same previously obtained sugar cane juice, after the steps of filtration, cake washing and pH adjustment, was fed to fermentation vats, in a batch setup, together with a *Clostridium acetobutylicum* inoculum. After the end of the fermentation, a leavened must was produced which contained 1.2% 1-butanol, 0.6% acetone and 0.2% ethanol, by weight, that was distilled to obtain 99% 1-butanol.

The 1-butanol so produced was then fed, at a 2 kg/h flowrate, to a dehydration system comprising 15 liter adiabatic reactors in series, each one fed with a gamma-alumina fixed bed catalyst. The 1-butanol stream was previously heated, so as to achieve the desired temperature of 360° C. at the entrance of the reactor. After the reaction, the output stream comprised a 77.5% molar 1-butylene and 20% molar 2-butylene geometric isomers mixture (inerts taking up the balance), which was purified by distillation and drying processes, obtaining polymeric grade 1-butylene. The 2-butylene isomers mixture, obtained as by-product, can be recycled and fed into an isomerization reactor for obtaining 1-butylene.

Figure 3:
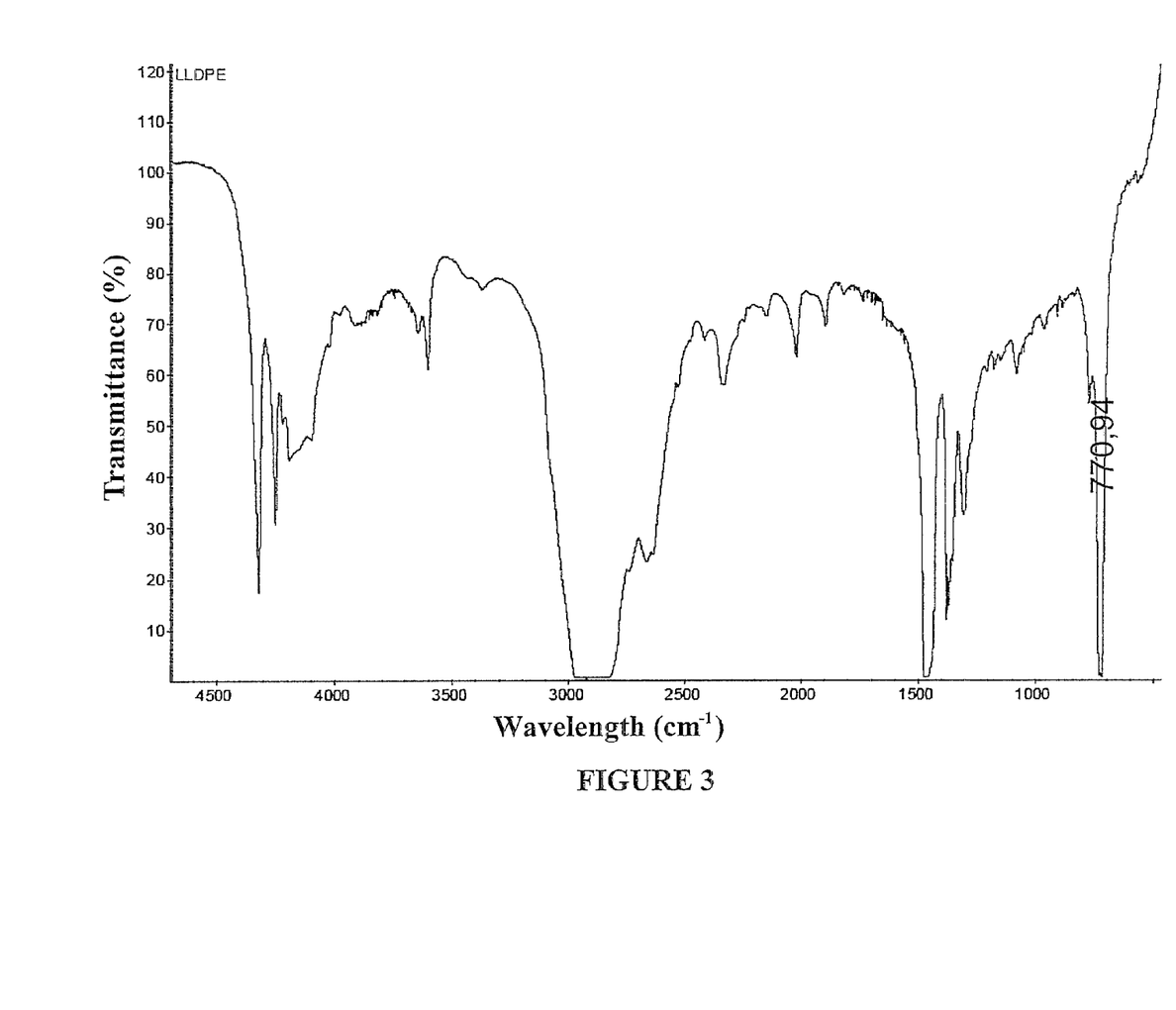
FIG. 3 shows the infrared spectrograph of a sample of the copolymer obtained from the Example of the Present Invention.

Step C: Production of Ethylene-Butylene Linear Low Density Copolymer with Ziegler-Natta Catalyst A suspension formed by n-hexane and 40 mg of Ziegler-Matta catalyst, triethyl-aluminum (TEAL), at an Al/Ti molar ratio of 400, and 600 mL of propane, was transferred to a 4 liter stainless steel reactor. Afterwards, the temperature was raised to 60° C. and an additional amount of 1000 mL of propane was fed to it. Soon after, the temperature was adjusted to 75° C., and the reactor was then fed with ethylene from Step A, at 700 kPa (7 bar); 300 mL of 1-butylene from Step B, and 300 kPa (3 bar) of hydrogen. The polymerization was carried out for 3 hours, during which the ethylene partial pressure was kept constant. The copolymer so obtained was dried in an oven at 60° C., and subsequently it was analyzed and certified according to ASTM D 6866-06 technical Norm, as containing carbon, which is 100% from a renewable carbon source. The copolymer so obtained was analyzed as regards fluidity index (FI) and density, according to technical ASTM D-1238 and ASTM D-1505 Norms, respectively. Incorporated butylene content was determined by infrared spectroscopy, as shown on FIG. 3, through butylene characteristic band at a 770 cm$^{-1}$ wavelength.

Table 1 below shows the results obtained with the example of the present invention and the properties of the copolymer as produced.

TABLE

| | Activity (kg Pol./g Cat.) | Density (g/cm$^3$) | FI 2.16 (g/10 min) | Butylene content (C$_4$) |
|---|---|---|---|---|
| Example of the Present Invention | 2.1 | 0.925 | 0.15 | 5.9% |

REFERENCE SIGNS LIST

Rule 11.13 (n) PCT

Equipment

1—Grinding or Diffusion and Filtration Unit
2—Vat
3—Vats
4—Distiller
5—Distiller
6—Dehydration Reactor
7—Dehydrogenation Reactor
8—Direct Synthesis Reactor
9—Distiller
10—Dimerization Reactor
11—Isomerization Reactor
12—Aldolic Condensation Reactor
13—Dehydration Reactor
14—Hydrogenation Reactor
15—Dehydration Reactor
16—Distiller
17—Isomerization Reactor
18—Polymerization Reactor
19—Waste Treatment Unit
20—Dehydration Reactor
21—Distiller
22—Isomerization Reactor
23—Distiller Inlet and Outlet Streams to the Copolymerization Processes Flowchart 1a. Sugar cane
1b. Water
2a. Sugar cane juice
2b. Sugar cane juice stream
2c. Sugar cane juice stream
3a. Leavened Must or Fermented Must
3b. Leavened Must or Fermented Must
3b. Leavened Must or Fermented Must
4a. Ethanol stream
5a. Ethanol stream
5b. Ethanol stream
5c. Ethanol stream
6a. Ethylene stream
6b. Ethylene stream
6c. Ethylene stream
6d. Ethylene stream
6e. Other products
6f. Other Products
6g. Unreacted ethanol stream
7a. 2-butylene isomers (mostly) stream
7b. 2-butylene isomers stream
7c. Other products
7d. Other products
8a. 1-butylene stream
8b. 1-butylene and 2-butylene isomers mixture stream
8c. 1-butylene stream
8e. 2-butylene isomers stream
8f. 1-butylene and 2-butylene isomers mixture stream
9a. Acetaldehyde stream
9b. 3-hydroxy-butanal stream
9c. Crotonaldehyde stream
9d. 1-butanol stream
9e. 1-butanol stream
9f. 1-butanol stream
9g. 1-butanol stream
9h. Unreacted 1-butanol stream
10a. 1-butylene, cis-2-butylene and trans-2-butylene mixture stream
11a. Ethylene-1-butylene copolymer
12a. Sugar cane husks
12b. Vinhoto
13a. Treated waste
14a. Catalyst
15a. Water
15b. Water
15c. Acetone and ethanol stream
16a. Ethanol and 1-butanol mixture stream
16b. Unreacted ethanol and 1-butanol mixture stream
17a. Ethylene and butylene isomers mixture stream
18a. Water
21a. 2-butylene isomers stream
21b. 1-butylene and 2-butylene isomers mixture stream
21c. Ethylene 1-butylene mixture stream

The invention claimed is:

1. An integrated process for the production of ethylene-butylene copolymers, 1-butylene being a comonomer, ethanol and the butanol being raw materials, which are obtained from vegetable sourced materials, via the fermentation of sugars extracted therefrom, comprising the steps of:
a) producing sugars through extraction and processing of the vegetable sourced raw materials;
b) feeding the sugar streams to a vat under ethanol producing must fermentation conditions;
c) distilling the ethanol containing leavened must stream in a distiller for the separation of ethanol;
d) dehydrating ethanol in the ethanol stream in a dehydration reactor, for obtaining an ethylene stream, to be purified in a distiller, producing ethylene to be fed to a reactor;
wherein said process further includes, in an integrated fashion, the following steps:
e) dehydrating a portion of the ethanol stream, in a dehydrogenation reactor, for obtaining an acetaldehyde and/or optionally feeding a portion of the ethanol stream to a direct synthesis reactor, for directly obtaining a 1-butanol stream;
f) aldolic condensation of the acetaldehyde stream from the dehydrogenation reactor, in a condensation reactor for obtaining a 3 hydroxy-butanol exit stream;
g) dehydrating 3 hydroxy-butanol from the condensation reactor, in a dehydration reactor to obtain a crotonaldehyde exit stream;
h) hydrogenating crotonaldehyde from the dehydrating reaction, in a hydrogenating reactor to obtain 1-butanol;
i) optionally, feeding sugar streams to vats, under 1-butanol producing must fermentation conditions;
j) distilling 1-butanol containing leavened must stream, in a distiller, for separating 1-butanol;
k) dehydrating 1-butanol from the 1-butanol stream, from step e), and/or from the 1-butanol stream, from step h), and/or from the mixtures thereof, and/or from the fermentation of sugars in steps i) and j), in the presence of alumina, silica, silico-alumina, zeolites and other metallic oxide catalysts, with a residence time varying from 0.1 to 60 seconds, and at temperatures ranging from 150° C. to 380° C., in an adiabatic or isothermic, fluidized or fixed bed dehydration reactor, for obtaining butylene isomers mixture;
l) distilling the butylene isomers mixture stream, from the dehydration reactor, in a distiller, which outputs the 1-butylene stream, and 2-butylene isomer streams;

m) isomerizing the 2-butylene isomers stream in the isomerization reactor, for obtaining the 1-butylene and 2-butylene isomer mixture stream which returns to the distiller; and n) polymerizing ethylene from the ethylene streams and 1-butylene from the 1-butylene stream, in the polymerization reactor, for obtaining the ethylene-butylene copolymer which has 100% renewable natural origin carbon.

2. The integrated process for the production of ethylene-butylene copolymers, with 1-butylene being the comonomer, and the ethanol and the butanol being the raw materials, which are obtained from vegetable sourced materials, via the fermentation of sugars extracted therefrom, which comprises steps (a), (b), (c), (i) and (j), according to claim 1, followed by the following steps:

k) simultaneous dehydrating ethanol and 1-butanol from the alcohols mixture, from ethanol and 1-butanol streams, in the presence of catalysts, such as alumina, silica, silico-alumina, zeolites, and metallic oxides, at temperatures ranging from 150° C. to 380° C., preferably from 250° C. to 370° C., and residence times of from 0.1 to 60 seconds, preferably from 1 to 30 seconds, in an adiabatic or isothermic, fluidized or fixed bed dehydration reactor, for obtaining the ethylene and butylenes mixture;

l) distilling the ethylene, 1-butylene and 2-butylene isomers mixture, from step k), in a distiller, that supplies a first ethylene and 1-butylene mixture stream and a second 2-butylene isomers stream;

m) isomerizing 2-butylene isomers stream, in an isomerization reactor, for obtaining 1-butylene and 2-butylene isomer streams; which returns to the distiller; and n) polymerizing the ethylene and 1-butylene from the first ethylene and 1-butylene mixture stream; in a polymerization reactor, to obtain the ethylene-butylene copolymer, which has 100% renewable natural origin carbon.

3. An integrated process for the production of ethylene-butylene copolymers, 1-butylene being a comonomer and ethanol being raw material, which is obtained from vegetable sourced materials, via fermentation of sugars extracted therefrom, comprising the following steps:

a) producing sugars through extraction and processing of vegetable sourced raw materials;

b) feeding sugar streams to a vat under ethanol producing must fermentation conditions;

c) distilling the ethanol containing leavened must stream, in a distiller, for separating the ethanol;

d) dehydrating ethanol from the ethanol stream, in a dehydration reactor, for obtaining an ethylene stream, to be purified in a distiller for obtaining ethylene to be fed to a reactor;

wherein said process includes, in an integrated fashion, the following steps:

e) dimerizing a portion of the ethylene stream, from step d), in a dimerization reactor for obtaining a 1-butylene and 2-butylene isomers mixture;

f) distilling the 1-butylene and 2-butylene isomer mixture, in a distiller for obtaining the 1-butylene stream and the 2-butylene isomer stream;

g) isomerizing the 2-butylene isomers stream, in an isomerization reactor, for obtaining a 1-butylene and 2-butylene isomer stream, which returns to the distiller;

h) polymerizing ethylene from the other portion of the ethylene from step d), and 1-butylene from the 1-butylene stream, from step f), in a polymerization reactor, for obtaining the ethylene-butylene copolymer which has 100% renewable natural origin carbon.

4. The process according to claim 1, wherein the sugars are dissolved sugars, hydrolyzed starch or hydrolyzed lignocellulosic components, and mixtures thereof.

5. The process according to claim 1, wherein *Saccharomyces cerevisiae* yeast is used in the fermentation of the sugars, for obtaining ethanol.

6. The process according to claim 1, wherein the ethanol obtaining steps, comprising the fermentation of sugars and subsequent leavened must distillation in the distiller, are adjusted such that the water ethanol molar ratio, in said steps are equivalent to the required feed to the dehydration reactor.

7. The process according to claim 1, wherein species of the *Clostidrium* gender bacteriae are used in the fermentation of sugars for obtaining butanol.

8. The process according to claim 1, wherein the dehydration step of ethanol or the ethanol and 1-butanol mixture is carried out in the presence of alumina, silica, silico-alumina, zeolites, and other metallic oxide catalysts, at temperatures of from 180° C. to 600° C., preferably from 300° C. to 500° C., in adiabatic or isothermic conditions, and a fluidized or fixed bed.

9. The process according to claim 1, wherein the 1-butanol dehydration step is carried out at residence times of from 1 to 30 seconds, and temperatures of from 250° C. to 370° C.

10. The process according to claim 1, wherein the isomerization step of 2-butylene in step (m) is carried out in the presence of hydrogen or basic catalysts or zeolites.

11. The process according to claim 3, wherein the dimerization step of ethylene in step (e) is carried out in the presence of nickel complexes, followed by distillation and isomerization of 2-butylene.

12. The process according to claim 1, wherein ethylene and 1-butylene polymerization, with 1-butylene as comonomer, is carried out in solution, in step (n) at temperatures ranging from 105° C. to 300° C., in the presence of Ziegler-Natta or metallocene catalysts.

13. The process according to claim 1, wherein the ethylene and 1-butylene polymerization, with 1-butylene as comonomer, is carried out in suspension, in step (n) at temperatures ranging from 50° C. to 100° C., in the presence of Ziegler-Natta or metallocene catalysts.

14. The process according to claim 1, wherein the ethylene and 1-butylene polymerization, with 1-butylene as comonomer, is carried out in the gas phase, in step (n) at temperatures ranging from 60° C. to 80° C., in the presence of Ziegler-Natta or metallocene catalysts.

15. The process according to claim 1, wherein the ethanol, butanol, ethylene and 1-butylene used in the steps of said integrated processes are vegetable sourced materials.

16. A process of using ethylene and 1-butylene in the production of ethylene-1-butylene copolymers, said ethylene and 1-butylene monomers obtained by a) producing sugars through extraction and processing of the vegetable sourced raw materials;

b) feeding the sugar streams to a vat under ethanol producing must fermentation conditions;

c) distilling the ethanol containing leavened must stream in a distiller for the separation of ethanol;

d) dehydrating ethanol in the ethanol stream in a dehydration reactor, for obtaining an ethylene stream, to be purified in a distiller, producing ethylene to be fed to a reactor;

wherein said process further includes, in an integrated fashion, the following steps:

e) dehydrating a portion of the ethanol stream, in a dehydrogenation reactor, for obtaining an acetaldehyde stream, and/or optionally feeding a portion of the ethanol stream to a direct synthesis reactor, for directly obtaining a 1-butanol stream;
f) aldolic condensing the acetaldehyde stream from the dehydrogenation reactor, in a condensation reactor for obtaining a 3 hydroxy-butanol exit stream;
g) dehydrating 3 hydroxy-butanol from the condensation reactor, in a dehydration reactor to obtain a crotonaldehyde exit stream;
h) hydrogenating crotonaldehyde from the dehydrating reaction, in a hydrogenating reactor to obtain 1-butanol;
i) optionally, feeding sugar streams to vats, under 1-butanol producing must fermentation conditions;
j) distilling 1-butanol containing leavened must stream, in a distiller, for separating 1-butanol;
k) dehydrating 1-butanol from the 1-butanol stream, from step e), and/or from the 1-butanol stream, from step h), and/or from the mixtures thereof, and/or from the fermentation of sugars in steps i) and j), in the presence of alumina, silica, silico-alumina, zeolites and other metallic oxide catalysts, with a residence time varying from 0.1 to 60 seconds, and at temperatures ranging from 150° C. to 380° C., in an adiabatic or isothermic, fluidized or fixed bed dehydration reactor, for obtaining butylene isomers mixture;
l) distilling the butylene isomers mixture stream, from the dehydration reactor, in a distiller, which outputs the 1-butylene stream, and 2-butylene isomer streams;
m) isomerizing the 2-butylene isomers stream in the isomerization reactor, for obtaining the 1-butylene and 2-butylene isomer mixture stream which returns to the distiller; and
n) polymerizing ethylene from the ethylene streams and 1-butylene from the 1-butylene stream, in the polymerization reactor, for obtaining the ethylene-butylene copolymer which has 100% renewable natural origin carbon.

17. A process of using ethylene and 1-buitylene in the production of ethylene-1-budylene copolomers, said ethylene and 1-butalene monomers obtained by
a) producing sugars through extraction and processing of the vegetable sourced raw materials;
b) feeding the sugar streams to a vat under ethanol producing must fermentation conditions;
c) distilling the ethanol containing leavened must stream in a distiller for the separation of ethanol;
d) optionally, feeding sugar streams to vats, under 1-butanol producing must fermentation conditions;
e) distilling 1-butanol containing leavened must stream, in a distiller, for separating 1-butanol;
f) simultaneous dehydrating ethanol and 1-butanol from the alcohols mixture, from ethanol and 1-butanol streams, in the presence of catalysts, such as alumina, silica, silico-alumina, zeolites, and metallic oxides, at temperatures ranging from 150° C. to 380° C., preferably from 250° C. to 370° C., and residence times of from 0.1 to 60 seconds, preferably from 1 to 30 seconds, in an adiabatic or isothermic, fluidized or fixed bed dehydration reactor, for obtaining the ethylene and butylenes mixture;
g) distilling the ethylene, 1-butylene and 2-butylene isomers mixture, from step k), in a distiller, that supplies a first ethylene and 1-butylene mixture stream and a second 2-butylene isomers stream;
h) isomerizing 2-butylene isomers stream, in an isomerization reactor, for obtaining 1-butylene and 2-butylene isomer streams; which returns to the distiller; and
i) polymerizing the ethylene and 1-butylene from the first ethylene and 1-butylene mixture stream; in a polymerization reactor, to obtain the ethylene-butylene copolymer, which has 100% renewable natural origin carbon.

18. A process of using ethylene and 1-butylene in the production of ethylene-1-butylene copolymers, said ethylene and 1-butylene monomers obtained by
a) producing sugars through extraction and processing of vegetable sourced raw materials;
b) feeding sugar streams to a vat under ethanol producing must fermentation conditions;
c) distilling the ethanol containing leavened must stream, in a distiller, for separating the ethanol;
d) dehydrating ethanol from the ethanol stream, in a dehydration reactor, for obtaining an ethylene stream, to be purified in a distiller for obtaining ethylene to be fed to a reactor;
wherein said process includes, in an integrated fashion, the following steps:
e) dimerizing a portion of the ethylene stream, from step d), in a dimerization reactor for obtaining a 1-butylene and 2-butylene isomers mixture;
f) distilling the 1-butylene and 2-butylene isomer mixture, in a distiller for obtaining the 1-butylene stream and the 2-butylene isomer stream;
g) isomerizing the 2-butylene isomers stream, in an isomerization reactor, for obtaining a 1-butylene and 2-butylene isomer stream, which returns to the distiller;
h) polymerizing ethylene from the other portion of the ethylene from step d), and 1-butylene from the 1-butylene stream, from step f), in a polymerization reactor, for obtaining the ethylene-butylene copolymer which has 100% renewable natural origin carbon.

* * * * *